United States Patent [19]
Sumanaweera et al.

[11] Patent Number: 5,967,987
[45] Date of Patent: Oct. 19, 1999

[54] ULTRASONIC SYSTEM AND METHOD FOR MEASUREMENT OF FLUID FLOW

[75] Inventors: Thilaka S. Sumanaweera, Palo Alto; Patrick J. Phillips, San Mateo, both of Calif.

[73] Assignee: Acuson Corporation, Mountain View, Calif.

[21] Appl. No.: 08/993,948

[22] Filed: Dec. 18, 1997

[51] Int. Cl.$^6$ ........................................... A61B 8/06
[52] U.S. Cl. ............................ 600/454; 600/465
[58] Field of Search ................... 600/443, 447, 600/454, 455, 462, 472

[56] References Cited

U.S. PATENT DOCUMENTS

| | | |
|---|---|---|
| 4,067,236 | 1/1978 | Hottinger . |
| 4,103,679 | 8/1978 | Aronson . |
| 4,265,126 | 5/1981 | Papadofrangakis et al. . |
| 4,373,533 | 2/1983 | Iinuma . |
| 4,790,322 | 12/1988 | Iinuma . |
| 5,515,857 | 5/1996 | Tsujino et al. . |
| 5,522,393 | 6/1996 | Phillips et al. . |
| 5,623,930 | 4/1997 | Wright et al. . |

OTHER PUBLICATIONS

Ding–Yu Fei et al., "Angle Independent Doppler Color Imaging: Determination Of Accuracy And A Method Of Display." Ultrasound in Med. & Biol., vol. 20, No. 2, pp. 147–155, (1994).

Charles F. Hottinger et al., "Blood Flow Measurement Using The Attenuation–Compensated Volume Flowmeter." Ultrasonics Imaging vol. 1, No. 1 (1979).

H. Tsujino, MS, et al., "Quantitative Measurement of Volume Flow Rate (Cardiac Output) by the Multibeam Doppler Method." Jounral of the American Society of Echocardiography, vol. 8, No. 5, Part 1 Sep.–Oct. (1995).

*Primary Examiner*—Francis J. Jaworski
*Assistant Examiner*—Ali M. Imam
*Attorney, Agent, or Firm*—Craig A. Summerfield; Brinks Hofer Gilson & Lione

[57] ABSTRACT

In an ultrasound system and method, a transducer connects to an estimator for obtaining first and second blood flow parameters associated with first and second scan line directions, respectively, in a first scan plane. One beam substantially covering a cross-sectional area of a tubular structure (uniform insonification) or a plurality of beams may be used. A first area associated with the cross-section of the tubular structure is also estimated from the blood flow parameters. The process is repeated for a plurality of scan planes. A processor determines the cross-sectional area of the tubular structure perpendicular to its axis (a second area), the average velocity of flow parallel to the axis, and the volume flow as a function of the first area and the first and second blood flow parameters of all the scan planes. For real-time volume flow, the orientation of the tubular structure is determined using the second area and the first and second blood flow parameters. As measurements are made, the orientation information is used to derive the real-time volume flow.

46 Claims, 2 Drawing Sheets

ULTRASONIC SYSTEM AND METHOD FOR MEASUREMENT OF FLUID FLOW

BACKGROUND OF THE INVENTION

This invention relates in general to ultrasound systems, and in particular to an ultrasound system for measuring fluid flow.

Volume flow measurements may be important for various medical diagnosis. Volume flow indicates blockage in blood vessels and the performance of diseased or transplanted organs. For example, changes in the blood flow out of a kidney over time may be determined. Other examples of clinical application of volume flow measurements include: blood flow through shunts, blood flow to or from transplanted or diseased organs, umbilical cord and uterine artery flow, flow through various arteries and vessels, the blood flow in the brachial artery before and after artificially induced ischemia, flow through mitral aortic tricuspid and pulmonic valves, and others.

Ultrasound systems have been used to estimate volume flow. For example, a mean velocity estimate for a small sample volume inside a vessel is obtained from spectral Doppler information. An angle of flow is estimated by user input. The user also manually outlines the vessel's cross section to obtain an estimate of area. The mean velocity, area and the appropriate trigonometric function of the Doppler angle are multiplied to obtain a flow estimate. However, the various manual tracings and estimations are laborious and prone to inaccuracies due to human error. Furthermore, obtaining the mean velocity from one sample volume may not accurately represent the true mean velocity across the entire vessel.

In another ultrasound technique for measuring volume flow, a high spatial resolution image is used to measure the flow profile across a vessel. The individual estimates of flow from each volume cell within a vessel are summed together to obtain the total volume flow. However, due to non-ideal ultrasound beam profiles, the information from one volume cell may duplicate, in part, another volume cell. Furthermore, this technique assumes that flow is parallel to the vessel or requires user estimation of the flow angle.

In yet another ultrasound technique to obtain volume flow, the velocity profile across a vessel is assumed to correspond to a particular function, such as a parabolic or plug profile. A single velocity estimate is obtained at the center of the vessel and used to estimate volume flow. The area of the vessel is calculated either manually or assumed to be circular. However, the area measurement is prone to human or estimation errors, and the actual flow profiles of fluids within a vessel may not match the parabolic or plug functions. Furthermore, as discussed above, the flow angle is manually entered, making the volume flow calculation laborious and error prone.

In yet another ultrasound technique for measuring volume flow, a cross section of a vessel located within a sample volume is insonified using a C-scan. Thus, ultrasound information is obtained from a plane parallel to the face of the transducer. In order to obtain the C-scans information, a fixed two-element transducer or a two-dimensional array transducer is used. The first moment of the C-scan information is calculated, eliminating the need to measure the area of the vessel. Measuring data in a plane parallel to the face of the transducer also eliminates the need to measure the flow direction. However, this technique does not accurately estimate volume flow in vessels that run parallel to the face of the transducer. Additionally, specialized transducers are required.

SUMMARY OF THE INVENTION

The present systems and methods may avoid many of the problems of the prior art. The various aspects of this invention provide for measuring the flow of fluid with an ultrasound system. Two examples of the various aspects of this invention are summarized below.

According to a first aspect of this invention, a transducer connects to an estimator for obtaining first and second blood flow parameters associated with first and second scan line directions, respectively, in a first scan plane. A processor determines a first area and volume flow as a function of the first area and the first and second blood flow parameters.

According to a second aspect of this invention, an orientation of fluid flow in the enclosed structure is determined as a function of a plurality of flow parameters associated with a plurality of scan planes, respectively, and as a function of at least one area measurement. A transducer is held in substantially one position while volume flow is calculated as a function of the orientation and measurements associated with the one position. The volume flow is displayed.

Further aspects and advantages of the invention are discussed below in conjunction with the preferred embodiments.

DETAILED DESCRIPTION OF PREFERRED EMBODIMENTS

Figure 1:
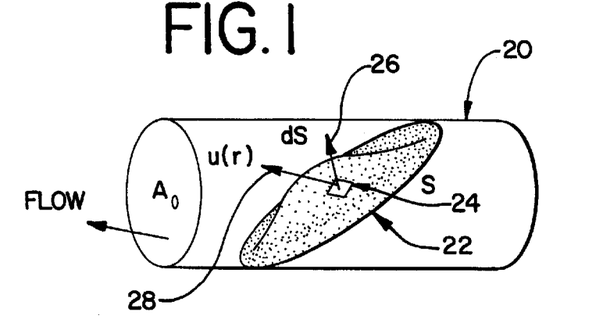
FIG. 1 is a schematic representation of an enclosed structure and a definition of flow.

The volume flow, as calculated by the preferred embodiments discussed below, is graphically represented in FIG. 1. An enclosed surface 20, such as an artery, vessel, shunt, chamber, or other bodily structure, is shown. An arbitrary surface, S, 22 is shown inside the enclosed structure 20. An area element, dS, 24 is shown on the arbitrary surface 22. A vector 26 normal to the arbitrary surface 22 at the area element 24 is also shown. The velocity of scatters, u(r), at any location on the arbitrary surface 22, such as the area element 24, is shown as vectors 28. The cross-sectional area of the enclosed structure 20 perpendicular to the axis of the enclosed structure 20 is designated as $A_0$. The volume flow, Q, through the arbitrary surface 22 is given by:

$$Q = \int_S u(r) \cdot dS = A_0 u_0, \quad (1)$$

where, $u_0$ is the mean velocity of scatters in a plane perpendicular to the axis of the enclosed structure 20, such as the plane defined by the smallest cross sectional area. Equation (1) is based on the assumption that there is no flow through the walls of the enclosed structure, and the flow passing through the arbitrary surface 22 must exit through the cross sectional area $A_0$.

The preferred embodiments described below are designed to provide accurate measurements of volume flow. The measurements are based on the three-dimensional orientation of the vessel in relation to a transducer. Ultrasound information associated with non-colinear scan lines in the same scan plane is obtained for two or more scan planes. The ultrasound information is used to measure average velocities and areas of an enclosed structure. Based on the trigonometric relationship of the vessel orientation to the scan plane, a relationship between the measured average velocities, and the measured areas is established. The volume flow is calculated from the relationship using a least squares error analysis.

Various ultrasound systems are capable of calculating the flow measurement as described above and detailed below. For example, an ultrasound system capable of obtaining Doppler velocity data along non-colinear scan lines and processing the data as discussed below may be used.

Figure 2:
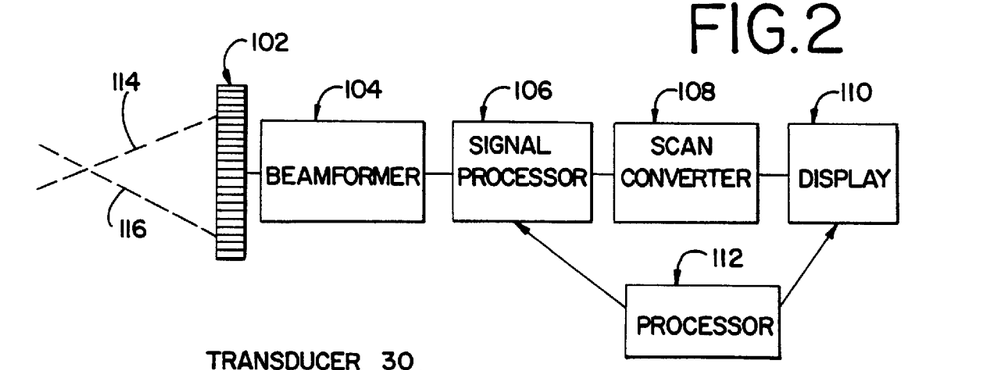
FIGS. 2 is a block diagram of an ultrasound system.

One embodiment of an ultrasound system for calculating volume flow is shown generally in FIG. 2 at 100. The system 100 includes a data path comprising a transducer 102, a beamformer 104, a signal processor 106, a scan converter 108 and a display device 110. A processor 112 is connected to the data path, preferably at least at the signal processor 106.

The transducer 102 is any of various transducers, such as a linear, 1.5 or 2 dimensional array of piezoelectric elements. The beamformer 104 is constructed as known in the art. The beamformer 104 may comprise separate transmit and receive beamformers. The beamformer 104 produces excitation signals for each of the elements of the transducer 102. The excitation signals are processed, such as by applying a relative delay or amplitude, to focus ultrasonic waveforms along one or more scan lines 114, 116. The scan lines may be at any of various angles relative to the transducer 102 and originate at various locations along the transducer 102. By transmitting a plurality of acoustic waveforms along a respective plurality of scan lines in various formats, such as linear or sector, a scan plane is sequentially insonified.

The acoustic waveforms are reflected off of structures within a body, including moving fluid within an enclosed structure, as echoes. The echoes are detected by the transducer 102 and provided as voltage signals to the beamformer 104. The beamformer 104 sums the voltage signals and outputs ultrasound data representative of the scan lines.

The signal processor 106 is a construction known in the art, such as a Doppler digital signal processors or filtering devices for providing Doppler estimates from the representative ultrasound data. The signal processor 106 may also include a parallel B-mode processor or spectral Doppler processor. A clutter filter may also be included. The signal processor 106 estimates the Doppler velocity, energy, and/or variance for each of various points or ranges along each scan line. The estimates and any B-mode information may be stored in a memory, such as a CINE memory.

The estimates, such as Doppler velocity, and/or any B-mode information representing the scan plane, are provided to the scan converter 108. The scan converter 108 is a processor for formatting the estimates into a Cartesian coordinate system for display.

The display device 110 is a monitor, such as a color monitor. The scan converted ultrasound data representing the scan plane is displayed on the display device 110 as a B-mode intensity, Doppler velocity, Doppler energy, Doppler variance or combination image.

The processor 112 is a digital signal processor or multi-purpose processor for calculating the volume flow from the Doppler velocity estimates. Alternatively, other hardware, such as an accumulator, summer and buffer data path, may also calculate the volume flow. The processor 112 obtains a frame of information, such as a frame of B-mode, Doppler velocity, Doppler energy, Doppler variance, or combinations thereof. The frame or frames of information include one or more values for calculating volume flow.

The processor 112 applies selection criteria to determine whether there is valid fluid flow data associated with each pixel or sample volume in the frame. Doppler values or B-mode values only or in combination are used to determine valid fluid flow. For example, if the amplitude of the B-mode signal associated with a pixel is high, a Doppler value for such pixel may not be a reliable indication of fluid flow. A low B-mode value and a high Doppler value indicates fluid flow. If the information corresponds to fluid flow, then the pixel is included in the calculation of volume flow. The number of pixels associated with valid fluid flow are counted. The velocities associated with such pixels are also summed. The processor performs the various calculations discussed below to derive the volume flow from the summed velocities and number of pixels. Alternatively, uniform insonification, as discussed below, may be used.

The calculated volume flow quantity, quantities, waveform and/or waveforms are provided to the display device 110. The calculated information is displayed with or separate from the B-mode or Doppler image.

The processor 112 may also provide control instructions to various components of the system 100. For example, the processor 112 controls the beamformer 104 to generate acoustic waveforms along scan lines 112, 114 in certain directions and scan formats. Alternatively, a separate processor provides control of the system 100.

The processor 112 or another processor may also coordinate user input. Thus, the user designates a region of interest on a displayed ultrasound image. The region of interest corresponds to pixels associated with the enclosed surface for calculation of volume flow. Alternatively, the region of interest is identified by applying one or more thresholds to the estimates or B-mode information as discussed above. The identified regions, regardless of the process of identification, are stored in the processor 112, another processor or a memory separate from the processor. Alternatively, the user configures the scan plane and associated image to be only the region of interest. The region of interest selection may be used, in addition or as an alternative to the valid fluid flow selection discussed above, for including or excluding velocity information and/or pixels from the summed velocity and/or the number of pixels.

Another preferred embodiment of an ultrasound system for calculating volume flow is disclosed in U.S. Pat. No. 5,623,930 (the '930 patent), the disclosure of which is herein incorporated by reference. The system disclosed, such as associated with FIG. 8 of the '930 patent, is programmed to perform the measurements and calculations described herein. Furthermore, a third accumulator data path may be used to perform the second velocity calculation discussed below.

Using one of the systems described above or another ultrasound system, the volume flow is determined. The user places the transducer 102 on a patient's skin and images an enclosed structure. Preferably, a Doppler mode is used for imaging but other modes, such as B-mode, may be used.

Figure 3:
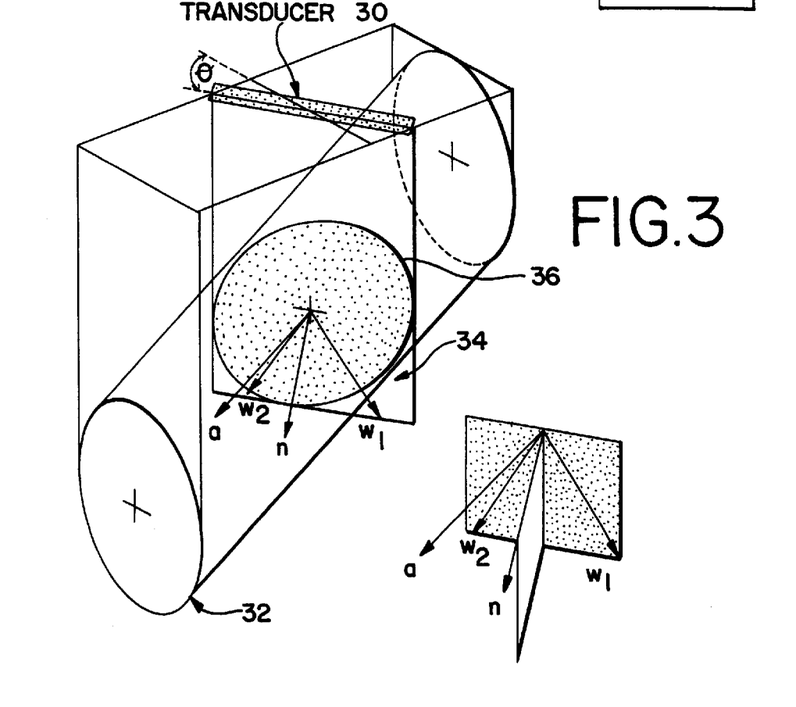
FIG. 3 is a schematic representation of the relationship between a scan plane and an enclosed structure.

Referring to FIG. 3, the method of one embodiment for determining volume flow is graphically represented. The transducer 30 is arbitrarily oriented to image an enclosed structure 32. Preferably, a cross section of the enclosed structure 32 is within the scan plane 34 (the enclosed structure 32 walls define a closed contour). The system 100

(FIG. 2) generates a series of ultrasound scan lines in a planar format, the scan plane 34. The system 100 interrogates the vessel along at least two directions, $w_1$, and $w_2$ in the scan plane 34. The scan plane 34 is defined by non-colinear unit vectors $w_1$, and $w_2$. The angle between $w_1$, and $w_2$ is represented as $\beta$. The intersection of the scan plane 34 and the enclosed structure 32 is represented by the shaded surface intersection 36. The intersection 36 is a cross-section of the enclosed structure 32. The cross-section associated with the intersection 36 is at any of various positions or angles relative to the enclosed structure 32 and the scan plane 34. The three-dimensional space corresponding to the scan plane 34 is further represented by the vector n which is normal to the scan plane 34.

The orientation of the enclosed structure 32 with respect to the three-dimensional space defined by $w_1$, $w_2$ and n is shown by the unit vector a. The direction cosines of unit vector a are:

$$h_1 = a \cdot w_1 = \frac{u_1}{u_0} \tag{2}$$

$$h_2 = a \cdot w_2 = \frac{u_2}{u_0} \text{ and} \tag{3}$$

$$h = a \cdot n = \frac{A_0}{A} \tag{4}$$

where $u_1$ and $u_2$ are the measured average velocities from one or more beams fired parallel to $w_1$ and $w_2$, respectively, and A is the area of the intersection 36. Furthermore, $u_0$ is the average velocity parallel to the unit vector a, and $A_0$ is the cross-sectional area perpendicular to the unit vector a.

Preferably, the transducer 30 is capable of obtaining two sets of data from the scan plane 34. The first and second sets are associated scan lines parallel to the unit vectors $w_1$ and $w_2$, respectively. For each set, one or more parallel beams scan the entire intersection 36.

Since $|a|=1$ and given the equations (2–4), it follows that:

$$h^2 + \frac{1}{\sin^2\beta}[h_1^2 + h_2^2 - 2h_1h_2\cos\beta] = 1. \tag{5}$$

Substituting for $h_1$, $h_2$ and h yields:

$$\left[\frac{A_0}{A}\right]^2 + \frac{1}{\sin^2\beta}\left\{\left[\frac{u_1}{u_0}\right]^2 + \left[\frac{u_2}{u_0}\right]^2 - 2\left[\frac{u_1}{u_0}\right]\left[\frac{u_2}{u_0}\right]\cos\beta\right\} = 1. \tag{6}$$

Figure 5:
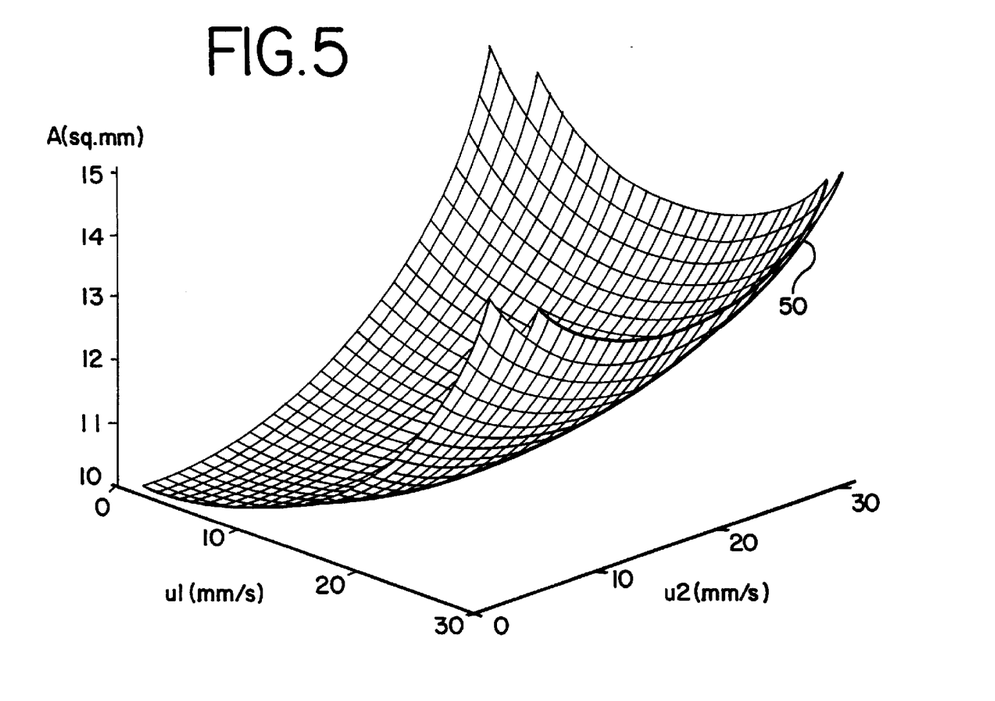
FIG. 5 is a schematic representation of a three-dimensional surface representing the measured vessel cross-sectional area as a function of measured velocities.

Referring to FIG. 5, the three-dimensional surface 50 given by equation (6) is shown. In equation (6), all of the quantities except $u_0$ and $A_0$ are either known or can be measured. The average velocity $u_1$ for the intersection 36 associated with beams fired parallel to $w_1$ is measured. The average velocity $u_2$ for the intersection 36 is also measured by firing ultrasound beams parallel to the unit vector $w_2$. Likewise, the area, A, of the intersection 36 is measured. The average velocities $u_1$ and $u_2$ are preferably obtained from blood flow parameter information, such as Doppler velocity. Other blood flow parameters providing velocity information may also be used.

Once the user orients the transducer 30, the user initiates the acquisition of these various measurements. The user may use a color velocity or an energy image to position the scan plane at an angle associated with non-zero velocity or energy estimates to improve volume flow accuracy. The user places an icon in the center of the display representation of the intersection 36 to designate the enclosed structure 32 and clicks on a button. Alternatively, the user may select a region of interest that encloses the intersection 36. Measurements are repetitively taken over a period of time, such as a fraction of a second, one or more seconds, or one or more heart cycles. More or fewer measurements may be obtained.

Various methods of transmitting and receiving ultrasonic waveforms may be used to measure the velocities $u_1$ and $u_2$. For example, ultrasound beams are transmitted and received along scan lines that are parallel to the unit vectors $w_1$ and $w_2$. In this example, firing of the ultrasonic beams associated with the unit vector $w_1$ are interleaved with firing the ultrasound beams associated with the unit vector $w_2$. The interleaving process continues until one or more frames of ultrasound information, such as information associated with the scan plane 34 for each unit vector $w_1$ and $w_2$ direction, are obtained. As another example, one or more ultrasound beams are transmitted in any of various directions, and the transducer receives along ultrasound scan lines parallel to $w_1$ and $w_2$ respectively. This multiple pulse chasing technique is disclosed in U.S. Pat. No. 5,522,393. As yet another alternative, a plurality of ultrasound beams are transmitted substantially simultaneously. A method and system for such transmissions is described in U.S. Pat. No. 5,675,554. The echo signals are received substantially simultaneously along a plurality of scan lines associated with the transmitted beams.

Based on the transmission and reception of ultrasound beams, blood flow parameters, such as Doppler velocity values associated with the intersection 36, are estimated. A variety of techniques may be used to calculate the average velocities $u_1$ and $u_2$ from the blood flow parameters. These techniques include autocorrelation estimation, fast-Fourier transform or cross correlation algorithms. Preferably, a pixel or range cell counting technique or a uniform insonification technique is used.

For the pixel or range cell (sample volume cell) counting technique, estimates of the Doppler velocity associated with various pixels or range cells within the scan plane 34 or intersection 36 are obtained for ultrasound beams parallel to each of the unit vector $w_1$ and $w_2$. Thus, two frames of Doppler velocity information are obtained. A sum of all of the estimates of Doppler velocity associated with the intersection 36 and a count of the number of pixels or range cells within the intersection 36 are obtained for each frame of information. To estimate the average velocities $u_1$ and $u_2$, the sum of Doppler velocity values are divided by the number of pixels for each frame. Preferably, the Doppler velocity information is used to determine the pixels or range cells within the intersection 36 associated with fluid flow. Other parameters, such as B-mode or Doppler energy, may be used to identify pixels associated with fluid flow.

The area, A, of the intersection 36 is determined by multiplying the count of the number of pixels associated with either unit vector $w_1$ or $w_2$ or an average of the counts associated with both unit vectors $w_1$ and $w_2$ by an area associated with each pixel. The area associated with each pixel is computed based on various display settings, as known in the art. Other techniques may be used to estimate the area, independent of the technique used to estimate the average velocities. The pixels included in the area are determined from color Doppler velocity, energy, velocity, or variance or B-mode information.

Figure 4A:
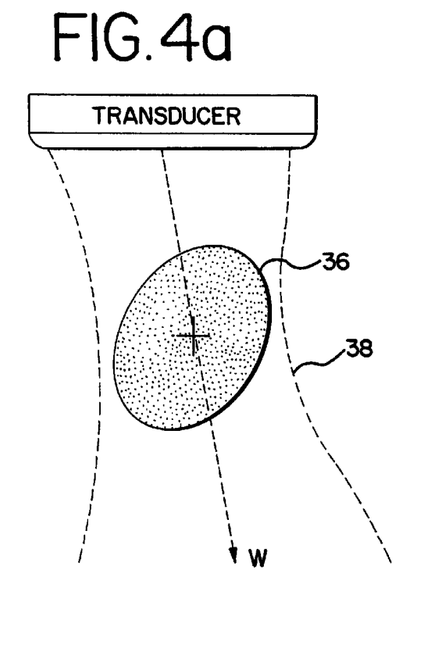
FIG. 4 is a schematic representation of two ultrasound beams with different beams widths interrogating a cross-sectional area.

Another technique for estimating the average velocities $u_1$ and $u_2$ and the area, A, is the uniform insonification technique. As represented by FIG. 4, two ultrasound beams 38 are used to estimate the average velocities $u_1$ and $u_2$. One beam 38 is fired parallel to unit vector $w_1$ and another beam 38 is fired parallel to the unit vector $w_2$. Each beam 38 is associated with a wide beam profile in the focal plane. Preferably, each beam 38 substantially covers the intersection 36. For example, points of the beam profile −6 dB from the peak (the dashed beam boarders) lay outside of the intersection 36. Substantially the entire intersection 36 with the enclosed structure is uniformly insonified. Preferably, for ranges corresponding to the intersection 36, the beam 38 does not intersect any moving fluids or structures not associated with the intersection 36.

The profile of the beam 38 is widened using various methods, such that the enclosed structure is uniformly insonified. For example, (1) a sinc apodization function is used to provide a wide rectangular beam profile pattern; (2) the aperture width associated with the beam 38 is appropriately adjusted; (3) low frequencies are used with the beam 38; or (4) the beam 38 is defocused, such as using appropriate delays. All four methods may be used together, and other methods for providing a wide beam profile may be used.

For each beam 38, the Doppler spectrum associated with the intersection 36 is computed. The power returned by scatterers having Doppler shifts between a first frequency $f_d$ and a second frequency, $f_d + df_d$, is represented by the function $P(f_d)df_d$. The average velocity is $$u = \frac{cM^1}{2f_cM^0}, \tag{7}$$

where, $M^0$ and $M^1$ are the zeroth and first moments of the Doppler spectrum $$M^0 = \int P(f_d)d f_d, \text{ and} \tag{8}$$

$$M^1 = \int f_d P(f_d) d f_d, \tag{9}$$

c is the speed of sound in tissue and $f_c$ is the center frequency associated with the beam 38.

Figure 4B:
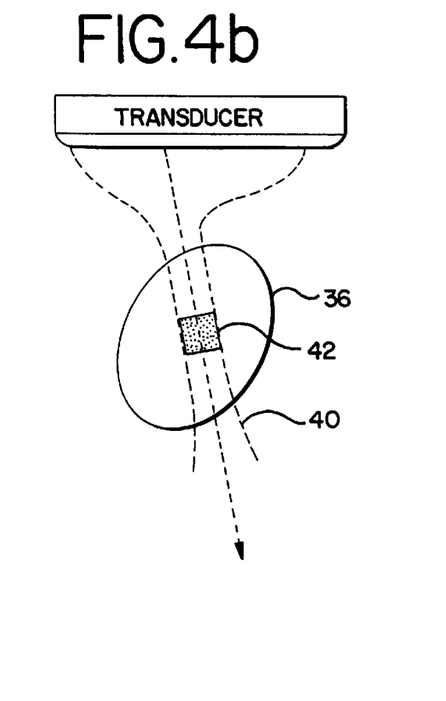

The area, A, of the intersection 36 is also estimated using the uniform insonification technique. Other techniques may be used to determine the area, independent of the techniques used to determine the average velocities $u_1$ and $u_2$. The area, A, is estimated by using the zeroth moment, $M^0$, calculated for either $u_1$ or $u_2$ or averaged for both $u_1$ and $u_2$ and a calibration beam as shown in FIG. 4b. The calibration beam 40 is associated with a width that is completely enclosed by the cross-section or intersection 36 of the enclosed structure. A sample, $A_c$, associated with the calibration beam 40 from within the intersection 36 is obtained by setting a gate size and the beam width. The zeroth moment of the Doppler spectrum associated with the sample 42 is calculated. The area, A, of the intersection 36 is given by:

$$A = A_c \frac{M^0}{M_c^0} \tag{10}$$

where, $M_c^0$ is the zeroth moment of the Doppler spectrum for the sample 42. In the system of FIG. 8 of the '930 patent, the microprocessor 120 obtains the zeroth moments from the F-mode processing unit 106.

Referring to FIG. 4, using any of the various techniques discussed above, the average velocities $u_1$ and $u_2$ and the associated area, A, of the intersection 36 are obtained for the scan plane 34. Preferably, two or more estimates of each of the average velocities $u_1$, $u_2$ and the area, A, of the intersection 36 are obtained for any given scan plane 34. For example, the average velocities $u_1$ and $u_2$ and A are measured over several cardiac cycles.

Measurements are obtained for two or more scan planes 34. The transducer 30 is moved so that the scan plane 34 intersects the enclosed structure 32 at a different orientation. For example, the transducer 30 is rotated, translated or slid to a second position such that the same general region of the enclosed structure is interrogated at a different orientation. Preferably, the transducer 30 is axially rotated (rotated about the center element of a linear array of elements). Additional values of the average velocities $u_1$ and $u_2$ and the intersection area A are measured for a scan plane 34 and intersection 36 associated with the second position. Preferably, the second scan plane intersects the enclosed structure 32 such that an enclosed area is within the scan plane.

The measurements of $u_1$ $u_2$ and A lie on a surface 50 as shown in FIG. 5. The surface 50 is used to estimate the cross section of the enclosed surface $A_0$ and the mean velocity $u_0$ of scatters in the plane perpendicular to the axis of flow. For example, let $$u = \frac{1}{\sin\beta}[u_1^2 + u_2^2 - 2u_1u_2\cos\beta]^{1/2}, \tag{11, 12, 13}$$

$$B = \frac{1}{A} \text{ and } B_0 = \frac{1}{A_0}$$

Using equations 11 through 13, equation 6 reduces to:

$$\left[\frac{B}{B_0}\right]^2 + \left[\frac{u}{u_0}\right]^2 = 1. \tag{14}$$

Equation 14 defines an ellipse with major and minor axes being $B_0$ and $u_0$, respectively.

Using the series of measurements of the average velocities $u_1$ and $u_2$ and the areas, A, associated with two or more positions of the transducer, estimates of the mean velocity $u_0$ and the inverse of the enclosed structures cross-sectional $A_0$ are optimized. Various techniques for least squares optimization may be used. The ellipse that minimizes the error cost function:

$$\Phi = \sum_{i=1}^{N}\left\{\left[\frac{B_i}{B_0}\right]^2 + \left[\frac{u_i}{u_0}\right]^2 - 1\right\}^2 \tag{15}$$

is given by:

$$\begin{bmatrix}\frac{1}{B_0^2} \\ \frac{1}{u_0^2}\end{bmatrix} = \begin{bmatrix}\sum B_i^4 & \sum B_i^2 u_i^2 \\ \sum B_i^2 u_i^2 & \sum u_i^4\end{bmatrix}^{-1} \begin{bmatrix}\sum B_i^2 \\ \sum u_i^2\end{bmatrix}, \tag{16}$$

where $B_i$ corresponds to the $i^{th}$ measurement of A and $u_i$ corresponds to the $i^{th}$ measurement of u. Using this method, the volume flow is calculated as:

$$Q = u_0/B_0. \tag{17}$$

A second method for optimizing accounts for the location of $T_i$ inside versus outside of the ellipse of equation (14), where $T_i$ is a series of velocity and inverse area measurements ($T_i=(u_i, B_i)$). If $T_i$ is some distance inside the ellipse, the cost contributed by $T_i$ in equation (15) is smaller than the cost contributed by $T_i$ of the same distance outside the ellipse. Therefore, the best fitting ellipse using the first method discussed above is larger than an ellipse associated with the actual flow. To eliminate this slight error, the second method is used. Using this second method, estimates to approximate $B_0$ and $u_0$ are calculated as described above from equation (16). These estimates are then refined based on the cost function for minimization:

$$\Psi = \sum_{i=1}^{N} d_i^2, \quad (18)$$

where, $d_i$ is the shortest distance between $T_i$ and the best fitting ellipse. The ellipse that minimizes the cost function of equation (18) is given by:

$$B_0 = \frac{\sum B_i \cos\theta_i}{\sum \cos^2\theta_i} \text{ and } u_0 = \frac{\sum u_i \sin\theta_i}{\sum \sin^2\theta_i}, \quad (19 \text{ and } 20)$$

$\theta_i$ is selected such that ($B_0 \cos\theta_i, u_0 \sin\theta_i$) corresponds to the point on the best fitting ellipse closest to $T_i$. Furthermore, $\theta_i$ satisfies:

$$u_0 u_i \cos\theta_i - B_0 B_i \sin\theta_i = (u_0^2 - B_0^2) \cos\theta_i \sin\theta_i. \quad (21)$$

Substituting $t = \tan\theta_i/2$ yields a forth order polynomial:

$$u_i u_0 t^4 + 2[B_i B_0 - (u_0^2 - B_0^2)]t^3 + 2[B_i B_0 - (u_0^2 - B_0^2)]t - u_i u_0 = 0, \quad (22)$$

Equation (22) has closed-form solutions given by the CRC Mathematical Tables. Using equation (22) and the estimates of $B_0$ and $u_0$ from the first method discussed above, $\theta_i$ is calculated. Using equations 19 and 20, $B_0$ and $u_0$ are calculated again based on $\theta_i$. As discussed in the first method above, the volume flow is equal to $u_0/B_0$.

If the flow through the enclosed structure 32 is pulsatile, both the cross-sectional area $A_0$ and the mean velocity $u_0$ may vary periodically. The shape of the surface 50 of FIG. 5 also varies periodically. To calculate the volume flow, a surface 50 for each of a plurality of set times in the pulsatile period is derived. The various measurements associated with each transducer orientation are used to derive surfaces 50 corresponding to the set times in the pulsatile period. For each transducer position P, a series of measurements $T_1^P, \ldots, T_{n_p}^P$, over several cardiac cycles are obtained, where $n_p$ is the number of measurements taken at each position of the transducer 30. Each of the $n_p$ measurements for one position of the transducer 30 may not correspond to the same time within the cardiac cycle as each of the $n_p$ measurements associated with a second transducer 30 position. For example, measurement $T_1^{P_1}$ (first transducer position, first measurement) occurs during diastole of the cardiac cycle, and the measurement $T_1^{P_2}$ (second transducer position, first measurement) occurs during systole of the cardiac cycle. The various measurement values within any given transducer position are registered and interpolated across time in order to obtain a set of values for each transducer position corresponding to set times within a cardiac cycle. A surface and the associated volume flow calculation for each set time within the cardiac cycle is performed from the measurements corresponding to the appropriate set time.

The resulting volume flows associated with each instant in time within the cardiac cycle may be averaged to obtain one volume flow quantity throughout the cardiac cycle. A waveform representing volume flow throughout one or more cardiac cycles may be calculated. The various instantaneous and averaged volume flow quantities and/or the waveforms of volume flow are displayed on the display device 110 (FIG. 2). Various other measured or calculated quantities, such as average velocities or areas, as instantaneous quantities, averages over a function of time, or waveforms, may also be displayed. The variance of the volume flow or any of the various velocities may be displayed as instantaneous or averaged volumes.

In another preferred embodiment, real time display of volume flow is accomplished by computing the direction cosines $h_1$, $h_2$ and h (equations 2, 3, and 4) of the unit vector a. After obtaining measurements associated with a plurality of scan planes and associated transducer positions, the transducer 30 is held in place. The transducer 30 may be held by hand or another device. $A_0$ and $u_0$ are calculated as discussed above. The direction cosines $h_1$, $h_2$ and h are computed using the calculated $A_0$ and $u_0$.

For pulsatile flow, the direction cosines are calculated for each of the various set instances in time within the cardiac or other cycle. Average direction cosines for each of the various instances within the cardiac cycle are determined as $$h_1 = \frac{\hat{h}_1}{\rho}, h_2 = \frac{\hat{h}_2}{\rho}, \text{ and } h = \frac{\hat{h}}{\rho} \text{ where}$$

$$\hat{h}_1 = \frac{1}{N_{\hat{p}}} \sum_{k=1}^{N_{\hat{p}}} h_{1k}, \hat{h}_2 = \frac{1}{N_{\hat{p}}} \sum_{k=1}^{N_{\hat{p}}} h_{2k}, \text{ and } \hat{h} = \frac{1}{N_{\hat{p}}} \sum_{k=1}^{N_{\hat{p}}} h_k$$

$$\rho = \left\{ \hat{h}^2 + \frac{1}{\sin^2\beta} \left[ \hat{h}_1^2 + \hat{h}_2^2 - 2\hat{h}_1 \hat{h}_2 \cos\beta \right] \right\}^{\frac{1}{2}},$$

where $N_{\hat{p}}$ is the number of measurements.

Once the enclosed structure 32 orientation is known by calculating the direction cosines, any number of beams along any number of directions are used to calculate the instantaneous mean velocity, the enclosed structure cross-sectional area and volume flow. This calculation is done at substantially the same time or a fraction of a second after transmitting the beams. For example, a single beam oriented along a unit vector w is used to estimate the instantaneous velocity u. The unit vector w is within the scan plane 34 defined by $w_1$ and $w_2$. The instantaneous volume flow is equal to $h/h_w Au$ where $h_w$ is equal to a·w. Vector a is determined from the direction cosines.

The microprocessor 112 outputs the real time instantaneous average velocity, cross-sectional area and/or volume flow as a quantity or an ongoing waveform to the display device 110. An ongoing average of the various instantaneous average velocities, cross-sectional areas and volume flows may also be displayed.

While the invention has been described above by reference to various embodiments, it will be understood that different changes and modifications can be made without departing from the scope of the invention. For example, dedicated hardware or multi-processors may be used for any of the various calculations. Additionally, differing formulas may be used to obtain the same or similar quantities.

It is therefore intended that the foregoing detailed description be understood as an illustration of the presently preferred embodiments of the invention, and not as a definition of the invention. It is only the following claims, including all equivalents, that are intended to define the scope of the invention.

What is claimed is:

1. A method for measuring flow of fluid in an enclosed structure with an ultrasound system, the method comprising the steps of:
   (a) obtaining first and second blood flow parameters representing a substantially same spatial location and associated with first and second scan line directions, respectively, in substantially a first scan plane;
   (b) determining a first area in the substantially first scan plane; and
   (c) determining volume flow as a function of the first area and the first and second blood flow parameters.

2. The method of claim 1 wherein the step (a) comprises obtaining Doppler velocity parameters.

3. The method of claim 1 wherein the step (a) comprises setting an angle between the first and second scan line directions.

4. The method of claim 3 wherein the step (a) comprises:
   (a1) transmitting at least a first beam in the first scan line direction; and
   (a2) transmitting at least a second beam in the second scan line direction.

5. The method of claim 3 wherein the step (a) comprises:
   (a1) receiving along at least one scan line in the first scan line direction; and
   (a2) receiving along at least one scan line in the second scan line direction.

6. The method of claim 4 wherein:
   the step (a1) comprises substantially covering the first area with the first beam; and
   the step (a2) comprises substantially covering the first area with the second beam.

7. The method of claim 6 wherein the step (a) comprises determining an average velocity from zeroth and first moments of a Doppler spectrum for each of the first and second beams, each Doppler spectrum associated with the first area.

8. The method of claim 7 wherein the step (a) for each of the first and second beams comprises:
   (a3) multiplying the first moment by a speed of sound in tissue;
   (a4) multiplying the zeroth moment by two and a center frequency associated with the first or second beam; and
   (a5) determining the average velocity as the result of step (a3) divided by the result of step (a4).

9. The method of claim 1 wherein:
   the step (a) comprises obtaining a plurality of the first and second blood flow parameters; and
   the step (c) comprises:
      (c1) averaging the plurality of first blood flow parameters; and
      (c2) averaging the plurality of second blood flow parameters.

10. The method of claim 1 wherein the step (b) comprises:
    (b1) counting a number of sample volume cells; and
    (b2) multiplying the number by a sample volume cell area.

11. The method of claim 6 wherein the step (b) comprises:
    (b1) obtaining a zeroth moment of a first Doppler spectrum associated with the first beam and the first area; and
    (b2) obtaining a zeroth moment of a second Doppler spectrum associated with a third beam and a second area, the third beam less wide than the first beam and corresponding to the second area, the second area within the first area.

12. The method of claim 11 wherein the step (b) comprises:
    (b3) multiplying the second area by the zeroth moment of the first Doppler spectrum; and
    (b4) dividing the result of step (b3) by the zeroth moment of the second Doppler spectrum.

13. The method of claim 1 wherein the step (c) comprises:
    (c1) determining a first average velocity as a function of the first and second blood flow parameters;
    (c2) determining a second area as a function of the first area; and
    (c3) multiplying the first average velocity by the second area.

14. The method of claim 13 wherein the steps (c1) and (c2) comprise fitting a second average velocity associated with the first blood flow parameters, a third average velocity associated with the second blood flow parameters and the first area into a surface.

15. The method of claim 14 wherein the steps (c1) and (c2) comprise performing a least squares error calculation.

16. The method of claim 15 wherein the steps (c1) and (c2) comprise minimizing an error cost function.

17. The method of claim 16 wherein the steps (c1) and (c2) comprise refining the minimization.

18. The method of claim 14 wherein the steps (c1) and (c2) comprise determining the first average velocity and the second area from the surface.

19. The method of claim 1 further comprising repeating at least the steps (a) and (b) for a plurality of scan planes.

20. The method of claim 1 further comprising the step (d) of displaying a volume flow quantity selected from the group consisting of: instantaneous volume flow, average volume flow, a waveform of volume flow as a function of time and combinations thereof.

21. The method of claim 13 further comprising the step (d) of displaying the volume flow, the first average velocity and the second area.

22. The method of claim 19:
    further comprising the step of obtaining a plurality of the first and second blood flow parameters and the first areas as a function of time for each of the plurality of scan planes; and
    wherein the step (c) comprises registering the plurality of the first and second blood flow parameters and the first areas associated with one of the plurality of scan planes as a function of time.

23. An ultrasonic apparatus for measuring flow of fluid in an enclosed structure, the apparatus comprising:
    (a) a transducer;
    (b) an estimator for obtaining first and second blood flow parameters representing a substantially same spatial location and associated with first and second scan line directions, respectively, in a scan plane; and
    (c) a processor for determining volume flow from a first area and the first and second blood flow parameters.

24. The apparatus of claim 23 wherein the processor sets an angle between the first and second scan line directions and determines a sample volume cell area.

25. The apparatus of claim 23 further comprising a beamformer for transmitting at least first and second beams associated with the first and second scan line directions, respectively, first and second widthes of the first and second beams, respectively, substantially covering the first area.

26. The apparatus of claim 23 wherein the processor determines an average velocity from at least zeroth and first moments of a Doppler spectrum for each of the first and second beams, each Doppler spectrum associated with the first area.

27. The apparatus of claim 24 wherein the processor counts a number of sample volume cells and multiplies the number by the sample volume cell area.

28. The apparatus of claim 27 wherein the processor determines the counted sample volume cells with data selected from the group of: Doppler data, B-mode data and combinations thereof, the determination responsive to a look-up-table.

29. The apparatus of claim 23 wherein the processor determines a first average velocity as a function of the first and second blood flow parameters, determines a second area from the first area, and multiplies the first average velocity by the second area.

30. The apparatus of claim 29 wherein the processor determines a second average velocity as a function of the first blood flow parameter, determines a third average velocity as a function of the second blood flow parameter, and determines the first average velocity as a function of the second and third average velocities.

31. The apparatus of claim 23 further comprising a display of at least the volume flow.

32. The apparatus of claim 23 further comprising a user input for designating the first area.

33. A method for measuring flow of fluid in an enclosed structure with an ultrasound system, the method comprising the steps of:
   (a) obtaining for each of at least two scan planes at least first and second blood flow parameters representing a substantially same spatial location and associated with first and second scan line directions, respectively;
   (b) determining for each of the at least two scan planes a first area;
   (c) calculating volume flow as a function of the first areas and the first and second blood flow parameters; and
   (d) displaying the volume flow.

34. The method of claim 33 wherein the step (a) comprises transmitting at least a first beam in the first scan line direction with a transducer selected from the group consisting of: linear, 1.5 and two dimensional arrays.

35. The method of claim 33 wherein the step (a) comprises:
   (a1) receiving along at least one scan line in the first scan line direction; and
   (a2) receiving along at least one scan line in the second scan line direction.

36. The method of claim 33 wherein the step (a) comprises obtaining the first and second blood flow as velocity values with a technique selected from the group consisting of: auto-correlation, Doppler and Fast-Fourier transform.

37. The method of claim 33 wherein the step (a) comprises generating the first and second blood flow parameters as first and second average velocities.

38. The method of claim 33 wherein the step (a) comprises the steps (a1), (a2) and (a3) for each of the at least first and second blood parameters of:
   (a1) multiplying a first moment of an echo signal spectrum by a speed of sound in tissue;
   (a2) multiplying a zeroth moment of the echo signal by two and a center frequency associated with the echo signal; and
   (a3) dividing a result of step (a1) by a result of step (a2).

39. The method of claim 33 wherein the step (a) for each of the first and second blood flow parameters comprises averaging velocity estimates for a plurality of regions within the enclosed structure.

40. The method of claim 33 wherein the step (b) comprises:
   (b1) determining pixels within the enclosed structure with data selected from the group consisting of: B-mode, Doppler energy, Doppler velocity, and Doppler variance data;
   (b2) counting a number of pixels within in the enclosed structure; and
   (b3) multiplying the number by a pixel area.

41. The method of claim 33 wherein the step (b) comprises:
   (b1) transmitting a first beam in a beam direction, a width of the first beam substantially covering a cross-section of the enclosed structure;
   (b2) transmitting a second beam in the beam direction, the width of the second beam within the cross-section and substantially the same as a width of a calibration area;
   (b3) gating first and second echo signals associated with the first and second beams respectively, the first echo signal gated to cover the cross-section and the second echo signal gated to be within the cross-section and substantially the same as a height of the calibration area; and
   (b4) determining the first area as a zeroth moment of the first echo signal multiplied by the calibration area and divided by a zeroth moment of the second echo signal.

42. The method of claim 33:
   further comprising the step of obtaining a plurality of the first and second blood flow parameters and the first areas as a function of time for each of the at least two scan planes; and
   wherein the step (c) comprises interpolating the plurality of the first and second blood flow parameters and the first areas associated with one of the at least two scan planes as a function of time.

43. The method of claim 42 wherein the step (c) comprises:
   (c1) obtaining the first and second blood flow parameters as average velocity estimates;
   (c2) obtaining the first and second blood flow parameters and the first areas at a series of set points in a cardiac cycle.

44. The method of claim 42 wherein the step (c) comprises:
   (c1) fitting first and second average velocities and the first area to a multi-dimensional function;
   (c2) minimizing a least squares error cost of the function; and
   (c3) estimating a cross-section area perpendicular to an axis of the enclosed structure and an average flow velocity along the axis.

45. The method of claim 44 wherein the step (c) comprises calculating the volume flow for each of a plurality of set times in a cardiac cycle as the cross-sectional area multiplied by the average flow.

46. The method of claim 33 wherein the step (d) comprises:
   (d1) displaying the volume flow as instantaneous and as time averaged values; and
   (d2) displaying instantaneous and time-averaged flow velocity and cross-sectional area.

* * * * *

UNITED STATES PATENT AND TRADEMARK OFFICE
CERTIFICATE OF CORRECTION

PATENT NO. : 5,967,987
DATED : October 19, 1999
INVENTOR(S) : T. S. Sumanaweera et al.

It is certified that error appears in the above-identified patent and that said Letters Patent is hereby corrected as shown below:

On The Title Page

In column 1, after line 5, please insert:

--5,174,295    12/1992    Christian et al.--.

In column 1, after line 8, please insert:

--5,779,641    7/1998    Hatfield et al.--.

In the Specification

In column 9, line 26, please change "$\theta_i$satisfies" to --$\theta_i$ satisfies--.

In column 10, line 47, please change "h/h$_w$Au" to --$\frac{h}{hw}$ Au--.

UNITED STATES PATENT AND TRADEMARK OFFICE
CERTIFICATE OF CORRECTION

PATENT NO. : 5,967,987
DATED : October 19, 1999
INVENTOR(S) : T. S. Sumanaweera et al.

It is certified that error appears in the above-identified patent and that said Letters Patent is hereby corrected as shown below:

In the Claims

In claim 44, line 1, please change "claim 42" to --claim 33--.

Signed and Sealed this

Fourteenth Day of November, 2000

Attest:

Q. TODD DICKINSON

Attesting Officer

Director of Patents and Trademarks